United States Patent
Lee et al.

(10) Patent No.: US 10,301,690 B2
(45) Date of Patent: May 28, 2019

(54) *STREPTOMYCES FILAMENTOSUS* VARIANT AND METHOD FOR PRODUCING DAPTOMYCIN USING SAME

(71) Applicant: DONG KOOK PHARM. CO., LTD., Seoul (KR)

(72) Inventors: Kang Hee Lee, Chungcheongbuk-do (KR); Kye Wan Lee, Seoul (KR); Kyung Hoi Cha, Gyeonggi-do (KR)

(73) Assignee: DONG KOOK PHARM CO., LTD., Seoul (KR)

( * ) Notice: Subject to any disclaimer, the term of this patent is extended or adjusted under 35 U.S.C. 154(b) by 194 days.

(21) Appl. No.: 15/105,826

(22) PCT Filed: Dec. 17, 2014

(86) PCT No.: PCT/KR2014/012457
§ 371 (c)(1),
(2) Date: Oct. 26, 2016

(87) PCT Pub. No.: WO2015/093839
PCT Pub. Date: Jun. 25, 2015

(65) Prior Publication Data
US 2017/0037484 A1  Feb. 9, 2017

(30) Foreign Application Priority Data
Dec. 18, 2013 (KR) .................. 10-2013-0158715

(51) Int. Cl.
| C12N 1/20 | (2006.01) |
| C07K 7/08 | (2006.01) |
| C12R 1/465 | (2006.01) |
| C12P 21/02 | (2006.01) |
| C07K 11/02 | (2006.01) |

(52) U.S. Cl.
CPC ................ *C12R 1/465* (2013.01); *C07K 7/08* (2013.01); *C07K 11/02* (2013.01); *C12N 1/20* (2013.01); *C12P 21/02* (2013.01)

(58) Field of Classification Search
None
See application file for complete search history.

(56) References Cited

U.S. PATENT DOCUMENTS 8,313,922 B2  11/2012  Bertetti et al.

FOREIGN PATENT DOCUMENTS

| CN | 101892287 A | 11/2010 |
| CN | 102965304 A | 3/2013 |
| KR | 10-1990-0008034 A | 6/1999 |
| KR | 10-1999-0066324 A | 8/1999 |
| KR | 10-2007-0054828 A | 5/2007 |
| KR | 10-2010-0039443 A | 4/2010 |
| KR | 10-2012-0058790 A | 6/2012 |

OTHER PUBLICATIONS

Miao et al., Microbiology (2005), 151, 1507-1523.*
Yu et al., Appl Biochem Biotechnol (2011) 163:729-743.*
Li et al. (Sep. 10, 2013) "improvement of Daptomycin Production in Streptomyces roseosporus through the Acquisition of Pleuromutilin Resistance", BioMed Research International. 2013:479742. pp. 1-8.
International Search Report corresponding to International Patent Application No. PCT/KR2014/012457, dated Mar. 24, 2015, 2 pages.
*Streptomyces* sp. Waksman and Henrici (ATCC 31568), ATCC, https://www.atcc.org/Products/All/31568.aspx?&p=1&rel=generalinformation, Aug. 21, 2018.

* cited by examiner

*Primary Examiner* — Irene Marx
(74) *Attorney, Agent, or Firm* — Lathrop Gage LLP; Andrew T. Wilkins

(57) ABSTRACT

Provided are a novel *streptomyces filamentosus* strain with improved daptomycin productivity, and a method for producing daptomycin using the same.

6 Claims, 1 Drawing Sheet

STREPTOMYCES FILAMENTOSUS VARIANT AND METHOD FOR PRODUCING DAPTOMYCIN USING SAME

RELATED APPLICATIONS

This application is a 35 U.S.C. § 371 filing of International Application No. PCT/KR2014/012457, filed Dec. 17, 2014, which claims priority to Korean Patent Application No. 10-2013-0158715, filed Dec. 18, 2013, each of which are incorporated herein by reference in their entireties.

TECHNICAL FIELD

The present disclosure relates to a novel *streptomyces filamentosus* strain with improved daptomycin productivity, and a method for producing daptomycin using the same.

BACKGROUND ART

Worldwidely, misuse or abuse of antibiotics for treating bacterial infections has led to the rapid growth of mutant bacteria, thereby increasing interest in developing novel classes of antibiotics having excellent efficacy as alternatives to the existing drugs. Of them, daptomycin is a cyclic lipopeptide material produced as a secondary metabolite by a soil actinomycetes, *streptomyces filamentosus*, also called *Streptomyces roseosporus*. Daptomycin has a structure consisting of 13 amino acids and coupling of decanoyl side chain to the N-terminal tryptophan. At present, daptomycin is approved as a therapeutic agent for complicated skin and skin structure infections (cSSSI) of Gram-positive pathogens. Due to a peculiar structure of the cyclic lipopeptide antibiotic, daptomycin binds to the cell wall of Gram-positive bacteria to cause depolarization. Daptomycin is a fast acting agent having an excellent bactericidal activity, but depends on import in the whole quantity.

Generally, wild-type strains isolated from natural sources show low productivity and produce similar materials in complex, and therefore, they are not suitable for the production of desired antibiotics. Accordingly, there is a demand for a method capable of producing antibiotics in a high yield. It was reported that a *streptomyces filamentosus* strain with improved daptomycin productivity can be developed by ribosome engineering in order to increase daptomycin productivity (Biomed Res Int. 2013, 2013, Article ID 479742). However, this method is used to develop a strain of which daptomycin productivity is improved only by about 30%, compared to a parent strain thereof. Accordingly, a demand for a strain having remarkably improved daptomycin productivity still remains.

DISCLOSURE

Technical Problem

The present inventors have made many efforts to develop a strain having improved daptomycin productivity, compared to a wild-type strain thereof. As a result, the present inventors developed a novel *streptomyces filamentosus* mutant strain having daptomycin productivity 12 times higher than that of the wild-type strain, and they also found that a commercial large-scale production of daptomycin is possible by optimizing the method for producing daptomycin using this strain, thereby completing the present invention.

Technical Solution

An object of the present invention is to provide a *streptomyces filamentosus* strain of Accession No. KCTC12267BP, in which the strain has a daptomycin productivity.

Another object of the present invention is to provide a use of the strain in the production of daptomycin.

Still another object of the present invention is to provide a method for producing daptomycin using the strain.

Advantageous Effects

A *streptomyces filamentosus* DKB108 strain according to the present invention has a greatly improved daptomycin high productivity, thereby providing pure daptomycin applicable to active pharmaceutical ingredients by large-scale tank fermentation. Accordingly, it is expected that the strain has a great ripple effect on the domestic and foreign markets for drugs against Gram-positive resistant bacteria, of which the whole quantity depends on import because of a monopolistic market structure.

BEST MODE

Figure 1:
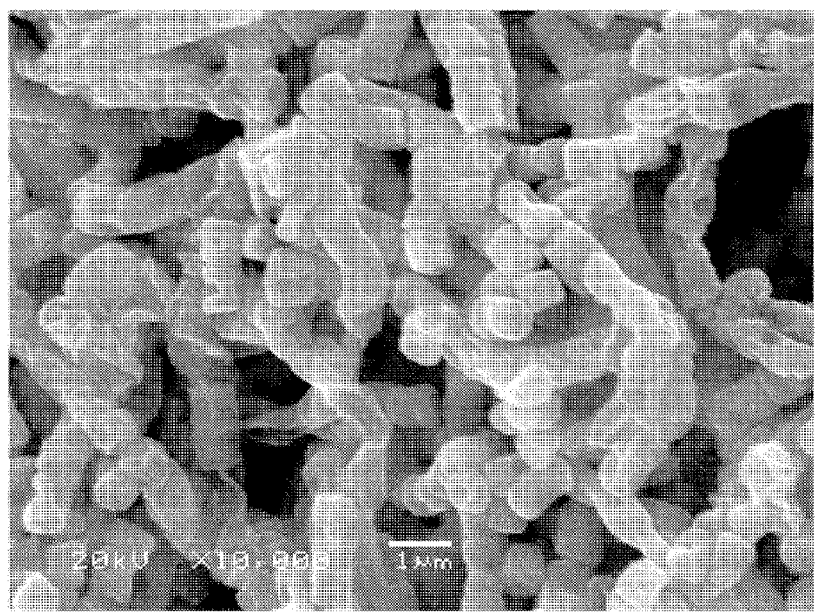
FIG. 1 is an image showing the morphology of DKB108 of the present invention.

An aspect of the present invention provides a *streptomyces filamentosus* strain of Accession No. KCTC12267BP, in which the strain has a daptomycin productivity.

As used herein, the term "daptomycin" refers to a lipopeptide antibiotic used for the treatment of life-threatening systemic infections caused by Gram-positive bacteria. Daptomycin is a member of the factor A-21978C0 type antibiotics and has a structure of the following Chemical Formula 1, in which a lipid moiety covalently linked to a peptide moiety is composed of a decanoyl side chain. Daptomycin is one of naturally occurring compounds found in a saprophytic soil bacterium, *streptomyces filamentosus*. Further, daptomycin is a safety-proven antibiotic compound, which is approved as a therapeutic agent for complicated skin and skin structure infections (cSSSI) of Gram-positive pathogens.

[Chemical Formula 1]

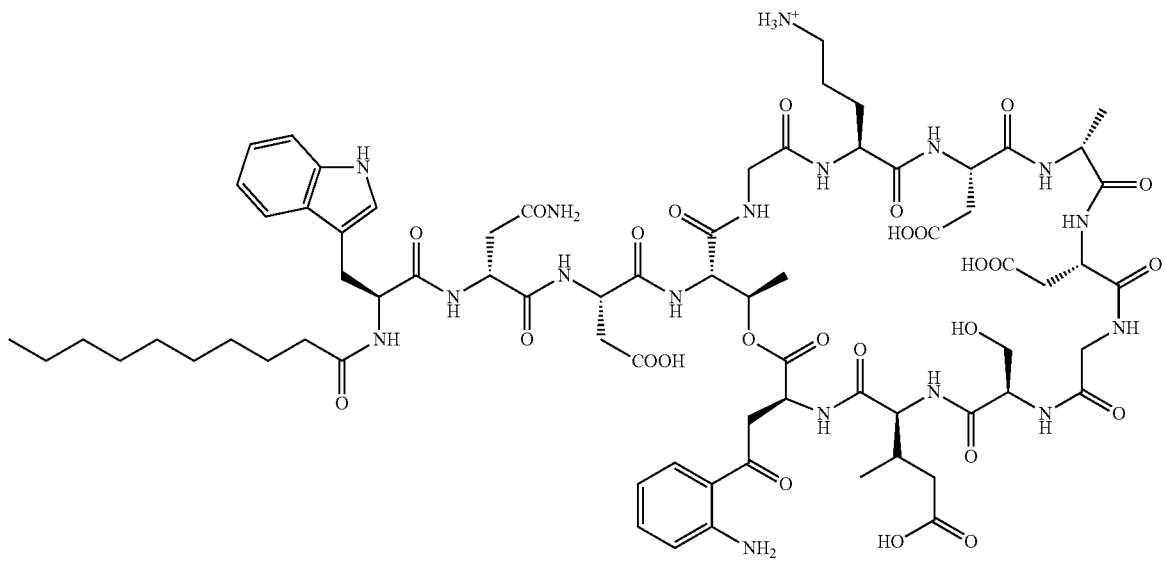

Daptomycin is an antibiotic against Gram-positive bacteria. Its bactericidal effect is excellent, but there is a difficulty in high-yield production thereof. In the present invention, accordingly, as a parent strain, *Streptomyces filamentosus* ATCC 31568 with daptomycin productivity, but the productivity is low, is subjected to UV irradiation and NTG mutation, thereby preparing a novel *Streptomyces filamentosus* mutant strain. The productivity of the antibiotic daptomycin was examined by measuring a growth inhibition zone of an indicator strain *Staphylococcus aureus*, that is, by applying a culture broth of the microorganism to an agar well to examine the effect. Then, excellent mutant strains were selected. Further, titer distributions of the mutant strains thus selected were continuously measured to block regression of the productivity of the excellent mutant strains due to spontaneous mutation. The mutant strains, of which safety is verified, were repeatedly subjected to artificial mutation to select mutant strains having improved productivity. The present inventors designated the selected *Streptomyces filamentosus* strain as DKB108, which was deposited to the Korean Collection for Type Cultures (KCTC) at the Korea Research Institute of Bioscience and Biotechnology (KRIBB), Deajeon, Republic of Korea, on Aug. 20, 2012, under the Budapest Treaty with the Accession No. KCTC12267BP (Example 1). DKB108 is a strain having daptomycin productivity 12 times higher than that of the parent strain, ATCC 31568. DKB108 produces daptomycin at a concentration of 2.75 g/L and also maintains high and stable daptomycin productivity even though subculturing is performed several times (Example 3). Upon tank fermentation, the production concentration was 2.75 g/L without a great change in the number of living microorganisms even at 209 hours after culture (Example 5), and therefore, the DKB108 strain of the present invention may be usefully applied to commercial production of daptomycin. In the present invention, DKB108 and KCTC12267BP may be used interchangeably.

The DKB108 strain has (1) morphological characteristics of showing an oval shape similar to cylinder arranged in chains, spore formation, Gram positive, dark pinkish gray colony formation; (2) physiological characteristics of tyrosine hydrolase −, urease +, amylase +, caseinase +, nitrate reductase +, gelatinase +, 8.5% NaCl tolerance +, melanin pigment formation on ISP-6 medium (−), melanin pigment formation on ISP-7 medium (+); and (3) characteristics of carbon source utilization: glucose +, xylose +, fructose +, inositol −, lactose −, sucrose +, mannitol +, arabinose −, raffinose +, galactose +, mannose +.

Specifically, the DKB108 strain has morphological characteristics of showing an oval shape similar to cylinder arranged in chains, spore formation, and aerobic, like the parent strain, but darker pinkish gray colony formation than that of the parent strain.

The DKB108 strain shows physiological characteristics of having no tyrosine hydrolase and producing enzymes such as urease, amylase, caseinase, amylase, nitrate reductase, and gelatinase, like the parent strain, but of surviving in 8.5% NaCl, unlike the parent strain that cannot survive in 8.5% NaCl. The DKB108 strain is melanin-negative on ISP-6 medium, like the parent strain, but forms dark purple soluble pigments on ISP-7 medium, unlike the parent strain that forms light purple pigments on ISP-7 medium.

In particular, the DKB108 strain of the present invention shows utilization of glucose, xylose, fructose, sucrose, mannitol, raffinose, galactose, and mannose as a carbon source in carbon source utilization patterns, but does not utilize inositol, lactose, and arabinose as a carbon source. There is a difference in the carbon source utilization patterns between the DKB108 strain and the parent strain utilizing lactose as a carbon source. That is, the DKB108 strain of the present invention shows different colony color, sodium chloride tolerance, and carbon source utilization from those of the parent strain.

Another aspect of the present invention provides use of the *streptomyces filamentosus* strain of Accession No. KCTC12267BP in the production of daptomycin.

The *streptomyces filamentosus* strain of Accession No. KCTC12267BP has daptomycin productivity, thereby being used in the production of daptomycin.

Still another aspect of the present invention provides a method for producing daptomycin, the method including the step of culturing the *streptomyces filamentosus* strain of Accession No. KCTC12267BP in a medium.

Further, the method may include the steps of culturing the strain in a medium; and recovering daptomycin from the cultured strain or the cultured medium.

As used herein, the term "culturing" refers to culturing of a microorganism under artificially controlled environmental conditions. A medium used for growing the DKB108 strain of the present invention may be any one of various culture mediums used in the art. However, for economic feasibility in production, optimum yield, and easy separation of a desired product from 12 or more related impurities reported in fermentation products, it is necessary to optimize a medium composition suitable for the production by using a specific medium. In large-scale tank fermentation for the production of daptomycin, media such as glucose, xylose, fructose, sucrose, maltose, mannose, cotton seed meal, soybean powder, corn steep liquor, yeast extract, dry yeast, methyl oleate, decanoic acid, glycerol, gluten, etc. may be used. As a preferred carbon source, a mixture of dextrin, molasses, and glucose is used. As a nitrogen source, amino acids such as dry yeast, soybean powder, soybean hydrate, cotton seed meal, corn steep liquor, gluten, and L-aspartic acid are useful, but yeast extract is preferred. For example, when the yeast extract used as a nitrogen source is replaced by dry yeast similar thereto, production of main related impurities of daptomycin is increased, and thus it is difficult to separate the desired product therefrom.

Hereinafter, optimum medium conditions and culture conditions for maximizing the production of daptomycin of the DKB108 strain of the preset invention are as follows.

In the method for producing daptomycin of the present invention, slant culture, seed culture, and main culture may be performed in this order for effective growth of the DKB108 strain. It is preferable that a stored strain is activated by slant culture and seed culture, followed by main culture.

The slant culture is a method of using a medium which is solidified in a slanted position, and a medium used in the slant culture may include 5 to 15 g/L of soybean powder, 2 to 6 g/L of yeast extract, 2 to 6 g/L of glucose, 0.5 to 3.5 g/L of calcium carbonate, and 15 to 20 g/L of agar.

The seed culture refers to culturing of a seed microorganism, which is added in a small amount for seed inoculation when the microorganism is cultured using a large amount of medium. In the present invention, the seed culture may be performed in a medium including 20 to 40 g/L of trypticase soy broth, 20 to 50 g/L of dextrin, and 1 to 5 g/L of yeast extract.

The main culture medium to examine a production amount of daptomycin may include 5 to 10 g/L of molasses, 5 to 15 g/L of glucose, 50 to 150 g/L of dextrin, 5 to 15 g/L of yeast extract, 2 to 10 g/L of gluten, and 0.5 to 5 g/L of mineral salts.

In the main culture step, an inoculation amount of the seed microorganism is restricted or seed of the homogenized pellet re-cultured under the same conditions is inoculated to minimize 12 or more daptomycin-related impurities. For example, when the inoculation amount of the homogenized pellet seed culture broth is about 0.1 to 2% of the volume of the main culture medium, production of the related impurities is greatly decreased.

The DKB108 strain shows a very high growth rate, and thus it is necessary to maintain aerobic conditions in water for the production of daptomycin. In the growth phase within hours after culture, a dissolved oxygen concentration should be maintained at 20% or higher. The DKB108 strain is a typical soil microorganism that grows at about 22° C. to 38° C., preferably 26 to 34° C., and the optimum temperature for daptomycin production is 28° C. and 31° C. Daptomycin production is preferably performed under conditions of a pH of 5.5 to 7.5, an agitation speed of 150 to 400 rpm, and an aeration rate of 0.5 to 1.5 vvm.

Daptomycin production occurs in the mid-exponential phase (PMV of 15% or more), and at this time, a precursor decanoic acid may be injected continuously to maximize the daptomycin production. The precursor decanoic acid may be injected in a solution form prepared by mixing decanoic acid with fatty acid methyl oleate or by mixing decanoic acid with an ammonia solution or glycerol.

Further, the method may include the step of recovering daptomycin from the cultured strain or the cultured medium.

As used herein, the term "cultured medium" means a product obtained by culturing the strain, and includes the cultured strain or no cultured strain. The cultured medium of the strain which is cultured to produce daptomycin is applied to a method which is generally used for isolation and purification of daptomycin, thereby recovering daptomycin. Examples of this method may include fractional crystallization, microfiltration, reverse osmosis, LPLC (Low Pressure Liquid Chromatography), HPLC (High Pressure Liquid Chromatography), FPLC (Fast Protein Liquid Chromatography), ion-exchange chromatography, gel filtration, reverse-phase chromatography, hydrophobic chromatography, or a combination thereof. As long as a method may be used to separate or purify daptomycin, the method is not limited thereto.

MODE FOR INVENTION

Hereinafter, the present invention will be described in more detail with reference to the following Examples. However, these Examples are for illustrative purposes only, and the invention is not intended to be limited by these Examples.

Example 1: Separation of Mutant Strain DKB108 by UV Irradiation

A parent strain, *streptomyces filamentosus* ATCC 31568 was cultured by slant culture at 30° C. for 12 days to collect spores, and then the spores were suspended in a physiological saline, followed by serial dilution of $10^{-2}$, $10^{-3}$, and $10^{-4}$, and plating on plate media. After pre-incubation at 30° C. for 2 hours, the plates were irradiated for 118 seconds in a glove box placed at a distance of 65 cm from two 20 W UV bulbs of 280 nm wavelength. In this regard, the death rate was 99.9%. To prevent repair by photoreactivation, light was immediately blocked out, and the plates were maintained at 4° C. for 2 hours. Colonies that survived on the agar plates at 30° C. for 6 days were collected, followed by seed culture and fermentation culture according to a method of the following Example 4. Fermentation was performed using a 500 ml-baffled flask in a shaking incubator under conditions of 30° C., 260 rpm for 7 days.

After completion of the culture, the culture broth was centrifuged. An agar-well method which is a biological detection method was used in order to examine growth inhibition of an indicator strain, *Staphylococcus aureus*. The agar-well method was applied to the analysis, because this method is an easy and simple method with lower errors, compared to other methods. This method is based on a principle that a diffusion rate is determined by a difference in a concentration gradient upon diffusion of a sample on an agar gel, and the radius of inhibition zone for a predetermined time is known to be proportional to the log of the concentration value. Based on this principle, antibiotic concentrations in unknown samples can be measured. This method was performed by the following procedure: before a trypticase soy broth agar medium solidified, the indicator strain *Staphylococcus aureus* was added thereto and uniformly suspended therein. The medium was poured into a test tube and allowed to solidify. Next, wells were punched into the agar using a stainless steel borer having a diameter of 5 mm, and agar in the well was suctioned by vacuum aspiration. The amount of the sample in the agar well was 130 µl, and a control group daptomycin was prepared and used in an amount of 0, 50, 100, 200, 300, and 1000 µg/ml.

The primary mutant strains selected by the agar-well method were subjected to secondary mutation using NTG (N-methyl-N'-nitro-N-nitrosoguanidine) under condition of a death rate of 70% in the same manner as in the above UV irradiation method. The mutant strains selected by the secondary mutation were subjected to fermentation by a method of Example 4, and a culture broth thereof was subjected to HPLC analysis and the biological detection method, agar-well method, thereby selecting mutant strains having excellent daptomycin productivity. The strains selected by the secondary mutation were repeatedly subjected to serial UV and NTG mutations twice or more to separate a mutant strain which has the highest daptomycin productivity and also stable daptomycin productivity even after several subcultures. The mutant strain was designated as DKB108, which was deposited to Korea Research Institute of Bioscience and Biotechnology on Aug. 20, 2012, under the Budapest Treaty with the Accession No. KCTC12267BP.

The results of the agar-well experiment of DKB108 investigated in the present invention are given in the following Table 1, and DKB108 of the present invention shows 1.5 times higher growth inhibition effect on *Staphylococcus aureus*, compared to the parent strain ATCC 31568.

TABLE 1

| | Daptomycin (mg/ml) | | | | | | | |
|---|---|---|---|---|---|---|---|---|
| | 0.00 | 0.05 | 0.10 | 0.20 | 0.30 | 1.00 | ATCC 31568 | DKB108 |
| Radius of inhibition zone (mm) | 5.00 | 8.60 | 10.60 | 12.00 | 13.20 | 16.00 | 10.2 | 15.2 |

Example 2: Characterization of Mutant Strain DKB108

The cultural, morphological, and physiological characteristics of the mutant strain DKB108 selected in Example 1 were examined.

The parent strain *streptomyces filamentosus* ATCC 31568 and the mutant strain DKB108 were cultured on a yeast extract•malt extract agar medium, an oat meal agar medium, an inorganic salt•starch agar medium, a glycerin•asparagine agar medium, a peptone•yeast extract•iron agar medium, and tyrosine agar medium at 30° C. for 4 days, and their growth was observed under an optical microscope and a scanning electron microscope. The characteristics thus observed are given in the following Table 2. Colors were described according to a document [Methuen Handbook of Colour, Methuen, London, 1978].

TABLE 2

| | Medium properties | |
|---|---|---|
| Medium | Parent strain (ATCC 31568) | Mutant strain DKB108 |
| Tryptone• yeast extract agar (ISP-1) | G: good<br>A: abundant<br>R: light brown<br>S: none | G: good<br>A: abundant<br>R: brown<br>S: none |
| Yeast extract• malt extract agar (ISP-2) | G: excellent<br>A: abundant<br>R: pinkish gray<br>S: light brown | G: excellent<br>A: abundant<br>R: pinkish gray<br>S: dark brown |
| Oat meal agar (ISP-3) | G: good<br>A: poor<br>R: colorless<br>S: none | G: good<br>A: poor<br>R: colorless<br>S: none |
| Inorganic salt• starch agar (ISP-4) | G: good<br>A: poor<br>R: light brown<br>S: none | G: good<br>A: poor<br>R: light brown<br>S: none |
| Glycerin• asparagin agar (ISP-5) | G: good<br>A: poor<br>R: brown<br>S: light brown | G: good<br>A: poor<br>R: dark brown<br>S: dark brown |
| Peptone• yeast extract• iron agar (ISP-6) | G: good<br>A: poor<br>R: colorless<br>S: none | G: good<br>A: poor<br>R: colorless<br>S: none |
| Tyrosine agar (ISP-7) | G: good<br>A: poor<br>R: colorless<br>S: light purple | G: good<br>A: poor<br>R: colorless<br>S: dark purple |

Abbreviation;
G: growth,
A: aerial hyphae,
R: reverse color,
S: soluble pigment

Common characteristics of the parent strain and the mutant strain DKB108 on ISP media are as follows. Hyphae morphology showed that spores were formed in an oval shape close to cylinder arranged in chains (FIG. 1) and positive in Gram staining according to Burgey's manual (1994). Good growths were observed on most ISP media. Poor aerial hyphae formation or no spore formation was observed on most media, except ISP-1 and ISP-2 media.

In contrast, the mutant strain DKB108 showed different reverse color and soluble pigment from the parent strain. The mutant strain DKB108 showed a dark reverse color on ISP-1 and ISP-5, compared to the parent strain, and a dark soluble pigment on ISP-2, ISP-5, and ISP-7, compared to the parent strain.

To examine physiological characteristics of the mutant strain *streptomyces filamentosus* DKB108 of the present invention and the parent strain *streptomyces filamentosus* ATCC 31568, they were plated on ISP (international *streptomyces* project) media. On the media, production of enzymes such as tyrosine hydrolase, urease, amylase, caseinase, amylase, nitrate reductase and gelatinase was examined by degradation of particular components. Osmotic tolerance against sodium chloride and melanoid production were also examined, and summarized in the following Table 3.

TABLE 3

| Characteristics | Streptomyces filamentosus ATCC 31568 | Streptomyces filamentosus DKB 108 |
|---|---|---|
| Morphology | Oval-shaped spores arranged in chains on hyphae | Oval-shaped spores arranged in chains on hyphae |
| Colony color | Pinkish gray | Dark pinkish gray |
| Gram staining | Positive | Positive |
| Oxygen demand | Aerobic | Aerobic |
| Melanin pigment | ISP6(−), ISP7(±) | ISP6(−), ISP7(+) |
| Tyrosine degradation | − | − |
| Urea degradation | + | + |
| Starch degradation | + | + |
| Casein degradation | + | + |
| Nitrate reduction | + | + |
| Protease activity | + | + |
| NaCl 0% | + | + |
| NaCl 4% | + | + |
| NaCl 7% | + | + |
| NaCl 8.5% | − | + |

−: below or negative reaction
+: above or positive reaction

TABLE 4

| Carbon source | Streptomyces filamentosus ATCC 31568 | Streptomyces filamentosus DKB108 |
|---|---|---|
| Glucose | + | + |
| Xylose | + | + |
| Fructose | + | + |
| Inositol | − | − |
| Lactose | + | − |
| Sucrose | + | + |
| Mannitol | + | + |
| Arabinose | − | − |
| Raffinose | + | + |
| Galactose | + | + |
| Mannose | + | + |

Slight differences in physiological characteristics between the mutant strain DKB108 and the parent strain are as follows.

The mutant strain DKB108 cultured on ISP-7 (Shinobu, 1958) plate medium for 21 days formed dark purple soluble pigments after 2 weeks, whereas the parent strain formed light purple pigments. However, both the parent strain and the mutant strain showed melanin negative on ISP-6 (Tresner and Danga, 1958) plate media.

The mutant strain DKB108 shows slightly different carbon source utilization patterns and osmotic tolerance from those of the parent strain. Carbon source utilization patterns showed the same patterns in the test using plate media containing Trptic soy broth (Difco™) and different carbon sources. However, the mutant strain DKB108 showed low growth in lactose utilization.

The results of liquid culture using a trypticase soy broth showed that in 8.125% sodium chloride, growth of the mutant strain DKB108 was observed, but no growth of the parent strain was observed. However, growth was observed in 6.5% sodium chloride liquid culture, indicating tolerance. In solid culture using a trypticase soy broth, the mutant strain DKB108 showed tolerance against 8.5% sodium chloride, whereas growth of the parent strain was inhibited. According to the ISP guideline, both the parent strain and the mutant strain were found to have tolerance against 7% sodium chloride (burgey's manual, 1994).

TLC showed that the cell wall of the mutant strain DKB108 was type-1 composed of LL-diaminopimelic acid and glycine.

The growth temperature of the strain was 24 to 37° C., and the optimal temperature for cell growth and daptomycin production was 30° C. Further, streptomyces filamentosus ATCC 31568 showed low daptomycin productivity and produced many related impurities in a lipopeptide complex form, whereas the mutant strain DKB108 produced daptomycin as a main biosynthetic metabolite. The carbon source utilization test was performed according to the method of Pridham, T. G and D. Gotrlib (J. Bacteriol., 56, pp. 107-114, 1948). After culturing at 30° C. for 12 days, they were examined. The results are given in the following Table 4.

These morphological and biochemical characterizations showed that the mutant strain streptomyces filamentosus DKB108 of the present invention showed patterns similar to those of the parent strain streptomyces filamentosus ATCC 31568, but there are slight differences in the size and color of colony formation, sodium chloride tolerance, and carbon source utilization.

Example 3: Test of Daptomycin Production of Mutant Strain DKB108

Daptomycin was quantified by using a column (Optimapak C8 4.6×250 mm, RStech co., Ltd.) and HPLC (Waters), and a freeze-dried daptomycin, CUBICIN® marketed by Cubist Pharmaceuticals, Inc was used as a standard material. A sample was prepared by centrifuging (5000 rpm, 15 min) the fermentation liquid, adding an equal amount of anhydrous ethanol to the supernatant, followed by centrifugation at 10,000 rpm for 5 minutes. The supernatant was filtered using a 0.45 µm filter, and used as a test liquid. For identification and quantification of daptomycin, 10 mg of the standard material was accurately weighed and dissolved in water to prepare 10 ml of the standard material. Liquid chromatography was performed according to the following procedure.

Detector: UV spectrophotometer (measurement wavelength: 214 nm)
Column: Optimapak C8 4.6×250 mm, RStech co., Ltd., RStech, Korea)
Flow rate: 1.5 ml/min
Auto injector temperature: 3-7° C.
Measurement range: 30 min
Sample injection: 20 µl
<Operating Condition 1>
Mobile phase: a ratio of mobile phase A and mobile phase B was controlled so that a peak maintenance time of daptomycin became about 15 minutes.
Mobile phase A: 9 g of ammonium dihydrogen phosphate was weighed and dissolved in 1500 mL of water. pH thereof was adjusted to 3.25 using 0.1 mol/L of phosphate, and water was added thereto to a volume of 2000 mL. 1000 mL of acetonitrile was added to 1000 mL of this solution.
Mobile phase B: 9 g of ammonium dihydrogen phosphate was weighed and dissolved in 1500 mL of water. pH thereof was adjusted to 3.25 using 0.1 mol/L of phosphate, and water was added thereto to a volume of 2000 mL. 400 mL of acetonitrile was added to 1600 mL of this solution.
<Operating Condition 2>
Mobile phase: a ratio of mobile phase A and mobile phase B was controlled so that a peak maintenance time of daptomycin became about 15 minutes.
Mobile phase A: 1000 mL of acetonitrile was added to 1000 mL of distilled water.
Mobile phase B: 9 g of ammonium acetate was weighed and dissolved in 1500 mL of water. pH thereof was adjusted to 3.25 using glacial acetic acid, and water was added thereto to a volume of 2000 mL. 400 mL of acetonitrile was added to 1600 mL of this solution.

Example 4: Production of Daptomycin by Mutant Strain DKB108

Step 1: Slant Culture

*Streptomyces filamentosus* mutant strain DKB108 stored by freeze-drying was used and inoculated on a sterile slant medium of the following Table 5, followed by static culture at 30° C. for 6 days.

TABLE 5

| Components | Concentration (g/L) |
| --- | --- |
| Soybean powder | 10 |
| Yeast extract | 4 |
| Glucose | 4 |
| Calcium carbonate | 2 |
| Agar | 20 |

Step 2: Seed Culture

Colonies showing abundant spore formation and gray and dark red brown color on the slant medium were collected and inoculated in 50 ml of a sterile growth activation medium of the following Table 6. The inoculated growth activation medium was cultured in a 500 ml-baffled flask at 30° C., 260 rpm for 24 hours.

TABLE 6

| Components | Concentration (g/L) |
| --- | --- |
| Trypticase soybean broth | 30 |
| Dextrin | 35 |
| Yeast extract | 3 |

Step 3: Main Culture

A culture broth cultured in the seed culture medium was inoculated at a concentration of 1% in 50 ml of a sterile main culture medium of the following Table 7. The inoculated main culture medium was cultured in a 500 ml-baffled Erlenmeyer flask at 30° C., 150~280 rpm for 8 days. The daptomycin production amount of the mutant strain DKB108 was 480 mg/L, which is 12 times higher than that of the parent strain (Table 8).

TABLE 7

| Components | Concentration (g/L) |
| --- | --- |
| Molasses | 7 |
| Glucose | 10 |
| Dextrin | 93 |
| Yeast extract | 10 |
| Fe(NH4)2SO4•7H2O | 0.5 |
| Gluten | 2 |

TABLE 8

| Strain | Daptomycin production concentration (mg/L) |
| --- | --- |
| *Streptomyces filamentosus* ATCC 31568 | 40 |
| *Streptomyces filamentosus* DKB108 | 480 |

Example 5: Tank Fermentation Production of Daptomycin by Mutant Strain DKB108

Figure 2:
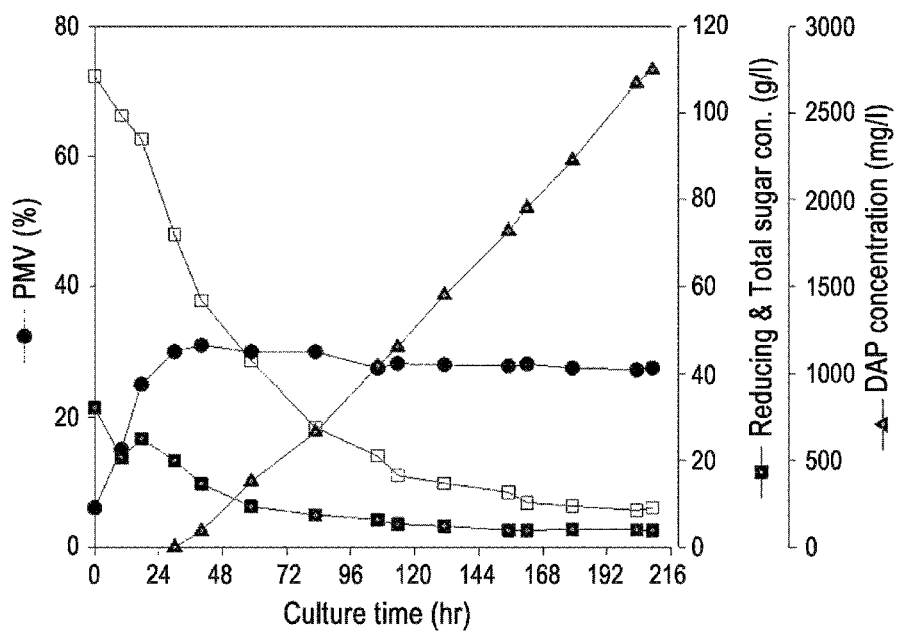
FIG. 2 shows changes in cell mass (packed mycelia volume, PMV), daptomycin concentration, and pH over time, when DKB108 of the present invention is cultured under optimized medium and temperature.

The seed culture broth obtained by the method of example 4 was inoculated at a concentration of 1% in 30 L of the sterile main culture medium of Table 7. This fermentation culture was performed in a 50 L-tank fermentor (kobiotech co., Korea) under conditions of 30° C., 1 vvm, pH 6.2~6.8 for 9 days. Dissolved oxygen (DO) in water was rapidly decreased according to cell growth, and therefore, to maintain DO of 20% or more, culture was performed by gradually increasing an agitation speed up to 400 rpm. At 30 hrs after culture, a 50% decanoic acid solution was continuously injected continuously, and fed-batch culture was stopped at a time when the culture broth pH increased. A daptomycin production amount of the mutant strain DKB108 was 2.75 g/L at 209 hrs after culture (FIG. 2).

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A modified *Streptomyces filamentosus* strain having daptomycin productivity, wherein the modified strain is deposited under Accession No. KCTC12267BP.

2. The strain of claim 1, wherein the strain has
   (1) morphological characteristics of showing an oval shape similar to cylinder arranged in chains, spore formation, Gram positive, dark pinkish gray colony formation;
   (2) physiological characteristics of tyrosine hydrolase –, urease +, amylase +, caseinase +, nitrate reductase +, gelatinase +, 8.5% NaCl tolerance +, melanin pigment formation on ISP-6 medium (–), melanin pigment formation on ISP-7 medium (+); and
   (3) characteristics of carbon source utilizations of glucose +, xylose +, fructose +, inositol –, lactose –, sucrose +, mannitol +, arabinose –, raffinose +, galactose +, mannose +.

3. A method for producing daptomycin, comprising the step of culturing the strain of claim 1 in a medium.

4. The method of claim 3, further comprising the step of recovering daptomycin from the cultured strain or the cultured medium.

5. The method of claim 3, wherein the step of culturing is performed slant culture, seed culture, and main culture in this order.

6. The method of claim 5, wherein the slant culture is performed in a medium comprising 5~15 g/L of soybean powder, 2~6 g/L of yeast extract, 2~6 g/L of glucose, 0.5~3.5 g/L of calcium carbonate, and 15~20 g/L of agar;
the seed culture is performed in a medium comprising 20~40 g/L of trypticase soybean broth, 20~50 g/L of dextrin, and 1~5 g/L of yeast extract; and the main culture is performed in a medium comprising 5~10 g/L of molasses, 5~15 g/L of glucose, 50~150 g/L of dextrin, 5~15 g/L of yeast extract, 2~10 g/L of gluten, and 0.5~5 g/L of inorganic salt under conditions of a seed inoculation amount of 0.1~2%, a temperature of 26~34° C., a pH of 5.5 to 7.5, an agitation speed of 150 to 400 rpm, and an aeration rate of 0.5 to 1.5 vvm.

* * * * *